United States Patent
Roulleau et al.

(10) Patent No.: US 6,661,518 B2
(45) Date of Patent: Dec. 9, 2003

(54) ANALYSIS MACHINE FOR ANALYZING A CLEANNESS CONDITION OF PERFORATED TRANSPARENT STRIPS

(75) Inventors: Guy M. Roulleau, Chalon sur Saone (FR); Michel Sacksteder, Chatenoy le Royal (FR)

(73) Assignee: Eastman Kodak Company, Rochester, NY (US)

( * ) Notice: Subject to any disclaimer, the term of this patent is extended or adjusted under 35 U.S.C. 154(b) by 252 days.

(21) Appl. No.: 09/947,554

(22) Filed: Sep. 6, 2001

(65) Prior Publication Data

US 2002/0030819 A1 Mar. 14, 2002

(30) Foreign Application Priority Data

Sep. 11, 2000 (FR) .............................. 00 11514

(51) Int. Cl.$^7$ ......................... G01N 21/84; G01N 21/00
(52) U.S. Cl. ...................... 356/430; 356/431; 356/443; 356/444
(58) Field of Search ................................ 356/430–431, 356/443–444

(56) References Cited

U.S. PATENT DOCUMENTS 4,709,157 A     11/1987   Shimizu et al.
5,426,509 A     6/1995    Peplinski
5,436,979 A  *  7/1995    Gray et al. .................. 356/443

FOREIGN PATENT DOCUMENTS

JP          04298354        10/1992

* cited by examiner

Primary Examiner—Frank G. Font
Assistant Examiner—Amanda Merlino
(74) Attorney, Agent, or Firm—David A. Novais

(57) ABSTRACT

An analysis machine for analyzing the cleanness condition of perforated strips enables a direct non-destructive measurement, without image conversion, of pollution by particles on the surface of plastic strips that are relatively transparent and perforated. This is done by using an automatic analysis machine, and a supporting and guiding device of the strips to be analyzed. The supporting and guiding device comprises a transparent revolving cylinder provided with at least one groove of small depth in which are arranged opaque masks that practically superimpose with the perforations of the strip to be analyzed. This arrangement prevents the disturbance and deterioration of the recording due to the light rays emitted by a light source located near the device.

4 Claims, 3 Drawing Sheets

ANALYSIS MACHINE FOR ANALYZING A CLEANNESS CONDITION OF PERFORATED TRANSPARENT STRIPS

FIELD OF THE INVENTION

The present invention relates to an analysis machine for analyzing the cleanness condition of relatively transparent strips that are used especially in the area of photography; and more specifically a device which permits a non-destructive analysis of the cleanness condition of the surfaces of perforated strips, in order to check whether the cleanness condition of these strips is satisfactory in view of the later use of the strips.

BACKGROUND OF THE INVENTION

There are many methods of detection and measurement of elements or particles that pollute or contaminate by adhesion surfaces or flat strips by adhesion, especially the surfaces of filmstrips or photographic papers.

U.S. Pat. No. 4,189,235 relates to a device that enables the dynamic measurement of the accumulation of dust in certain zones of a barely transparent banknote. The banknote to be tested is positioned between an optical system comprising a light source and a receiving optical system comprising a microscope and photodiodes. The light emitted towards the receiving cell depends on the amount of dust accumulated on the inspected zone. The light is transformed into an electrical signal by a transducer and the electrical signal is analyzed, to determine the number and quantity of dust accumulated in the inspected zone of the banknote.

U.S. Pat. No. 4,669,885 discloses a process and a system of optical inspection that enable the direct, rapid and comparison-free detection of unwanted particles that adhere in particular to semiconductor or printed circuit plates. The principle is based on an optical device comprising sources of light, laser rays, or x-rays and projection and detection means enabling an image of the inspected printed circuit to be obtained; thus enabling the identification, according to the indices of reflection and transmission, of the following elements: the plate having unwanted matter, the positioning of each particle of unwanted matter on the plate, and especially on the lines making up the printed circuit. The usefulness of this method and the associated means is to measure accurately the faults rapidly and directly on the production line for semiconductor plates.

U.S. Pat. No. 5,033,095 discloses a process and a device to automatically determine and quantify the value of the particles the pollute sheets used in the paper industry. The strip of material to be inspected is passed manually or automatically into a scanner type image analyzer, in order to produce an image that is then computer analyzed line by line to enable, via an analog-digital conversion module, the comparative line by line measurement of each pixel of the image, and then the detection of whether the continuity between two successive lines is normal or not, which is based on defining a recognized and preset acceptance threshold or level for the particles appearing on the analyzed image. Data concerning the particles that pollute the paper sheets is stored in a memory, which can be classified by preset categories, and a paper report concerning these particles can be produced.

U.S. Pat. No. 5,402,228 discloses a process and a device that enable the measurement and recording of the size and intensity of small dust type marks or faults appearing on a paper strip. The method uses a dust counter that comprises in particular a device enabling the holding of the paper strip to be inspected, an optical system and CCD (charge couple device) sensors linked to an electronic computer. An analysis process, starting with the recording of analog image data in a database, and using digital image conversion, enables the comparison of the digital image of the inspected paper strip with preset references of values of marks or dust stored in the computer's memory. A histogram linked to the condemning dust marks is constructed from the database and reference thresholds, thus enabling the analysis of the pollution rates of the inspected paper strips.

U.S. Pat. No. 5,436,979 discloses an improvement of the processes previously in existence, especially described in U.S. Pat. No. 4,189,235 and U.S. Pat. No. 5,033,095, in the sense that it enables the measurement, by quantification and characterization, of anomalies such as dust and scratches remaining on the surface of a sample of photographic film, after the sample of photographic film has undergone a cleaning procedure; in order to verify the efficiency of the cleaning procedure. U.S. Pat. No. 5,436,979 describes a reliable and robust automatic process that using a scanner and a computer enables noise or variations of luminous intensity or lighting occurring in time to be allowed for when measuring, especially between two consecutive measurements; by reconditioning the original image, so that variations of luminosity not coming from the anomalies to be measured are eliminated from the reconstituted image to be analyzed that then only contains the anomalies. This method, improved by comparison with the previous state of the art, is based on a digital electronic processing process of the scanned image that enables noise or lighting variations to be eliminated.

The processes and devices described in the above mentioned patents that use as a base a means of lighting the sample of the strip to be inspected, come up against a significant problem when perforated strips are inspected, in the sense that the light source transmits luminous rays into the perforations, which constitutes a major disturbing element for the measurement of the anomalies, especially near these perforations, and going well beyond the simples light variations referred to in U.S. Pat. No. 5,436,979. In the case of dust measurements to be carried out on perforated strips, it is preferable to practically completely get rid of significant disturbance or noise due to the emitted light rays that cross the perforations made in the strips to be analyzed and that strongly disturb the measurements, and to do this without even having to use, for instance, digital-analog conversion means of the perforated filmstrip analyzed.

SUMMARY OF THE INVENTION

The present invention overcomes the above-noted problem by enabling a fast, efficient and accurate measurement to be made, without image conversion or processing, of the pollution by particle of the surface of perforated strips, by using a specific device for supporting and guiding the strip to be analyzed. The device enables the practically complete masking of the perforations made in the strip when it passes through the automatic analysis machine, and thus enables the detection and analysis of the anomalies due to the unwanted particles deposited abnormally on the whole surface of the analyzed strips.

The present invention relates to an automatic machine for analyzing a surface cleanness condition of relatively transparent strips. The machine comprises a structure and electromechanical components adapted to hold and convey at least one strip to be analyzed; a light source adapted to light the at least one strip; a recording device adapted to detect, record and view the surface of the at least one strip; and a supporting and guiding device for supporting and guiding the at least one strip while in a lighting and recording zone. The supporting and guiding device enabling a substantial masking of perforations made in the at least one strip, when it runs in the automatic machine.

BRIEF DESCRIPTION OF THE DRAWINGS

Other particular characteristics and advantages of the present invention will become apparent in the detailed description of particular embodiments, as illustrated in the following annexed drawings.

DETAILED DESCRIPTION OF THE INVENTION

The following detailed description according to the particular embodiments of the invention refers to the drawings in which the same numerical references identify the same structural items, in each of the various figures.

With reference to these drawings, an automatic analysis machine for analyzing the cleanness condition of the surface of strips enables the verification of the cleanness of samples of magnetic tape or relatively transparent photographic films. The photographic films are for instance strips of unused, exposed (gray-tint film) or developed film. The machine enables the detection of the number, position and size of the dust particles on the analyzed strips.

Apart from a supporting and guiding device, the machine comprises a structure 42 or a chassis to house, hold or support electromechanical components 44 such as electric motors, speed controller and guide rollers for at least one filmstrip. It is clear that a machine can be designed to enable the analysis of several strips at the same time, the strips being arranged in a parallel side by side arrangement. The electromechanical components enable the running of strip(s) 30 to be assured from at least one payout cylinder to at least one take-up cylinder; in good kinematic conditions, i.e. with synchronization of the whole maintaining correct tension of the filmstrip(s) 30. In the rest of the description, "strip 30" will be referred to, but this reference includes all the single or multi strips configurations arranged parallel on the machine. The machine also comprises a device for lighting (light source 20) the strip 30 to be analyzed and a device for detection, recording and viewing. The machine also comprises a management program and an electronic device that enable partly the display of the optical density curves of the analyzed strip 30 according to the width of the strip 30, and partly, the management of work files of the analyzed strip 30.

Figure 1:
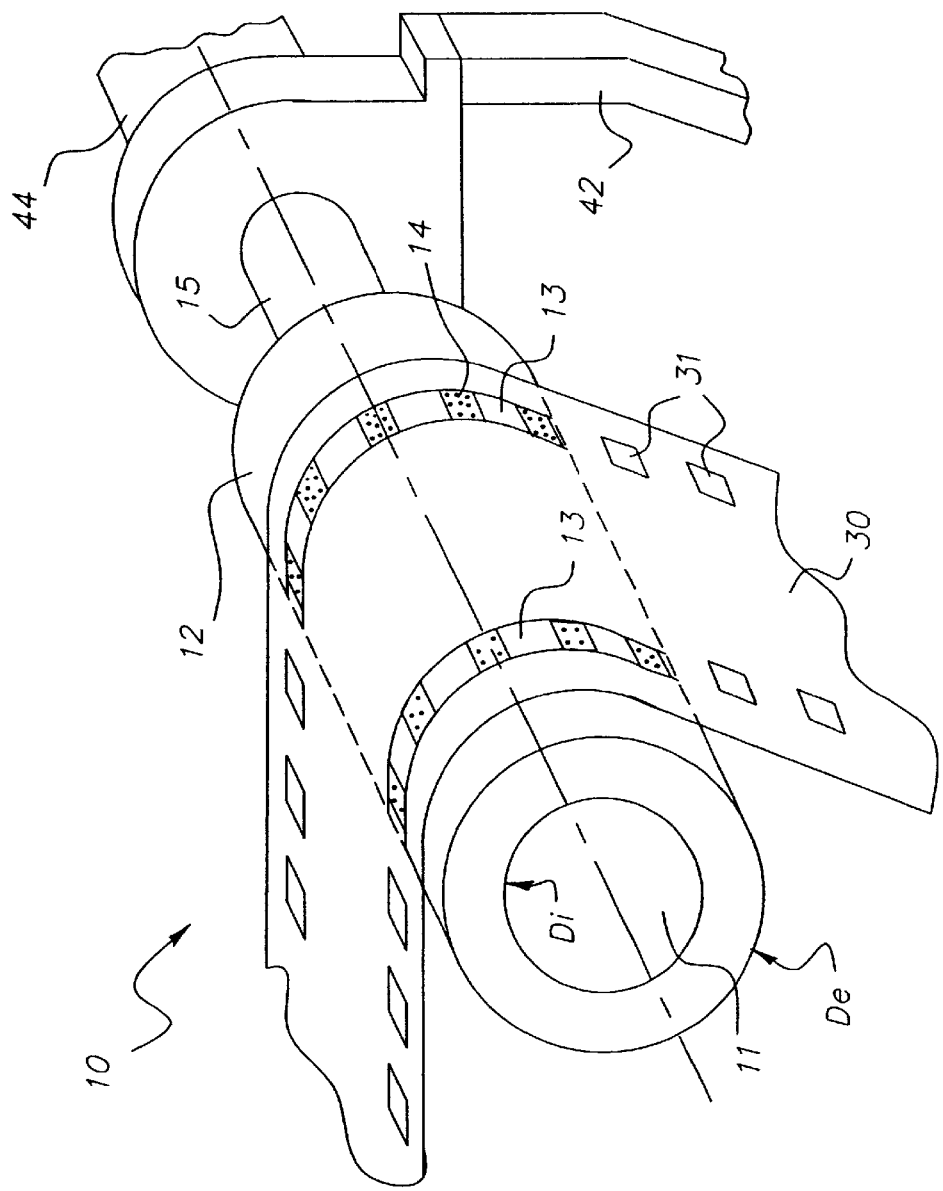
FIG. 1 represents a view of a strip support and a guiding device.
Figure 2:
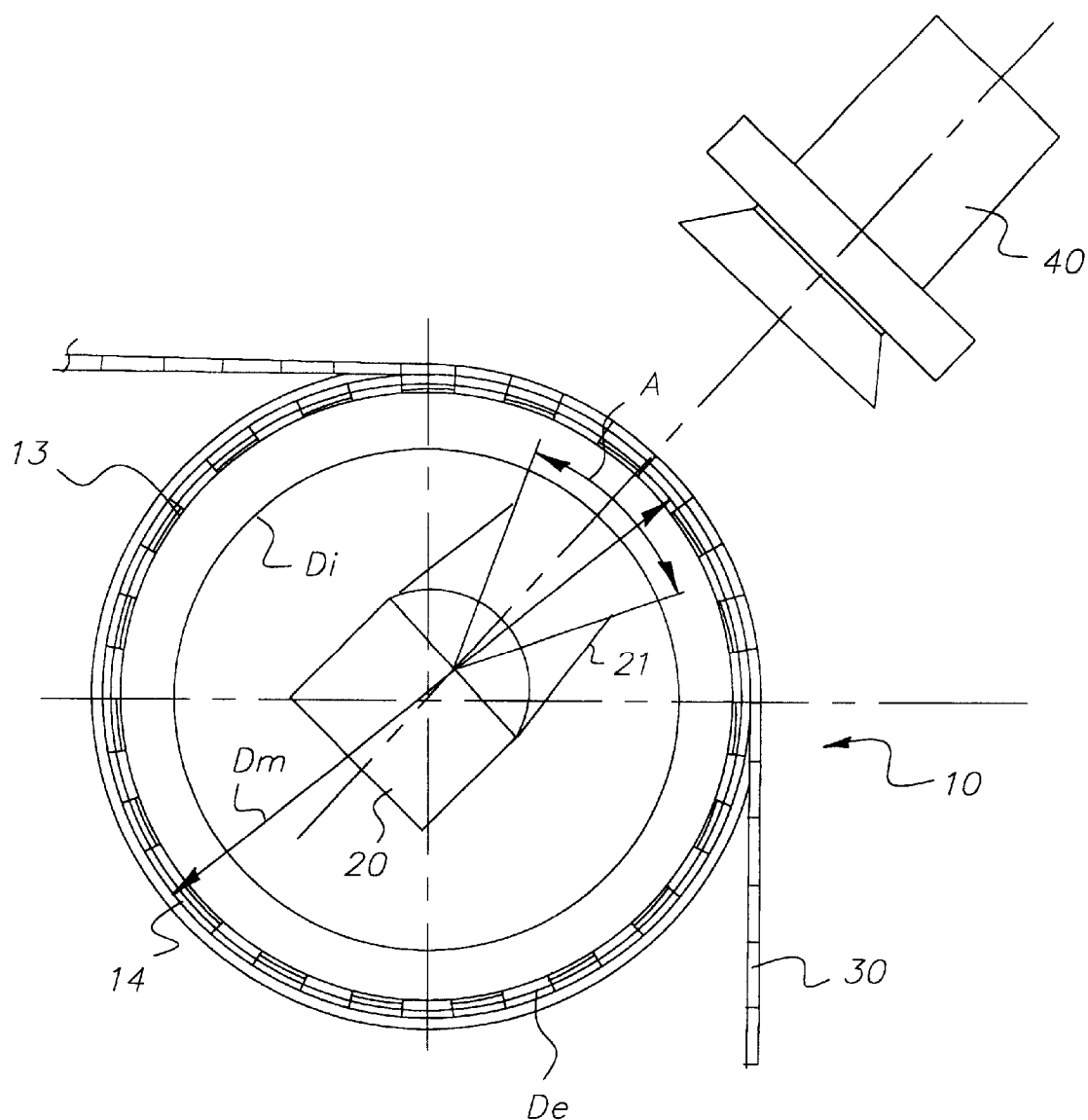
FIG. 2 represents a view representing the main components of the analysis machine for strip cleanness conditions.

FIG. 1 corresponds to a preferred embodiment of the supporting and guiding device 10 of the strip 30 to be analyzed comprising a revolving cylinder 12, in transparent material, driven in rotation by a shaft 15, which is coaxial with it. The cylinder 12 can be for instance made of plastic and fitted with a means of angular encoding, by cylindrical sectors, with the encoding means being linked to the machine's management program; in order to process the non homogeneous surface and transmission elements inherent to plastic. In one preferred embodiment, the cylinder 12 is glass. The external surface of the cylinder 12 is mirror polished with conservation of the shape of revolution according to a tolerance of less than 0.05 mm and preferably less than 5 micrometers; compared with the diameter producing this external surface. The external surface of the cylinder 12 comprises at least one groove 13 intended to be registered with the perforation line(s) of the strip 30. The groove 13 is concentric with the external surface of the cylinder 12. If there is more than one groove 13, the grooves are parallel to one another. The groove 13 is less than 1 mm deep and its width corresponds practically with the width of the perforations of the strip 30. If there is more than one groove, the distance between the axes of the grooves 13 corresponds practically to the distance between the perforations of the strip 30, applied to the external surface of the cylinder 12; the application being arranged so that the main axis of the analyzed strip 30 is practically perpendicular to the axis of the cylinder 12, as shown in FIG. 1. Opaque masks 14, for instance of synthetic material, are vacuum placed so that they are practically superimposed on perforations 31 of the strip 30 to be analyzed; which is to prevent significant disturbance and deterioration of the recording and thus of the later analysis; the disturbance and deterioration being due to the light rays crossing the perforations of the filmstrip 30 to be analyzed and that dazzle the recording means. The thickness of the masks 14 is such that the diameter Dm referenced on FIG. 2 and created by the thickness of the masks is less by several hundredths of a millimeter than the diameter De, referenced on FIG. 2, of the external surface of the cylinder 12; which is to prevent abrasion problems of the strip 30 which presses on the external surface of the cylinder 12. The optical density of the masks 14 is more than or equal to the density of the analyzed strip 30.

It is clear that the opaque masks 14 can be formed by a thin layer of photographic emulsion distributed homogeneously on the appropriate parts of the bottom of each groove 13, with the emulsion layer becoming opaque, after processing following its exposure to a light source.

Shaft 15 is for instance servo-linked to a drive system enabling the strip 30 to run, so that there is very accurate synchronization enabling, according to the speed variations, continuous superimposition during the analysis phase, of the perforations of the strip 30 with the thin layer masks 14 placed in the grooves 13. An interior 11 of the cylinder 12 is cut out with a cylinder of revolution of diameter Di, referenced on FIG. 2, coaxial with the axis of the cylinder 12 and mirror polished with shape conservation. A cut out or opening 11 enables the installation of the light source 20; the coaxial state of the external surface of the cylinder 12 given by De, and the cut out 11 given by Di, is preferred in order to limit the angle of diffusion of the light emitted by the light source 20 to the exterior of the cylinder 12; which is according to the envelope angle A referenced on FIG. 2, the angle A being practically between 1 and 1.5 radians. A system comprising at least one detector of strip 30 running to register the running or length of strip 30 analyzed and a recording device or recorder 40 of the strip 30 image, enables data collection; the relative position of the recording device 40 in relation to the device 10 is such that the recording device 40 is placed practically in a zone of the space swept by the cone of light diffused according to angle A. This zone, comprising the light source 20, the cylinder 12 and the recording device 40 can be referred to as the lighting and recording zone. The system enables the collection of the data for analysis, i.e. especially the number and position of the particles deposited on the analyzed strip 30. The data is then processed electronically to enable the generation of a curve characterizing the pollution of the analyzed strip 30, with the curve being viewable, classified by means of a file management system and recovered at any moment by using the means that are preferably a viewing screen 50, a control keyboard 60, a printer 70, as referenced on FIG. 3c. It is clear that by replacing a single curve, a mapping can be performed that is representative of the optical density and/or dust distribution.

According to a variant that is not illustrated of this preferred embodiment of the device 10 and the associated means, the light source 20 in the cut out 11 inside the cylinder 12, can comprise a means of integral sphere type, having an opening to let light through and obtain a homogeneous light line serving as a source.

Another variant that is not illustrated of this preferred embodiment of the device 10 and the associated means includes reversing the positions of the light source 20 and recording device 40 in relation to the device 10, by placing the light source 20 outside the cylinder 12 and the recording device 40 inside the cut out 11. For reasons of size and space available in the cut out 11, for instance a digital recording means comprising linear CCD sensors can be placed in the cut out 11.

Another variant that is not illustrated of this preferred embodiment of the device 10 includes making the groove 13 and the thin layer opaque masks 14, inside the cylinder 12 and with diameter Di; the opaque masks 14 are arranged and dimensioned in the groove 13 so that the light rays that cross the perforations of the film to be analyzed are stopped by the opaque masks 14. In this way, the difference in thickness that corresponds to the half sum (De–Di) is allowed for.

Another variant that is not illustrated of this preferred embodiment of the device 10 includes extending the principle of placing the opaque masks in the crown zones of the cylinder 12, the crown zones that can be limited by the edges of the analyzed strip 30 when the strip 30 is applied to the cylinder 12; as a result, the opaque crown zones are located practically on either side of the edges of the analyzed strip 30, outside the strip. It is clear that the position of the opaque masks enable analysis of determined zones of the strips 30.

Figure 3A:
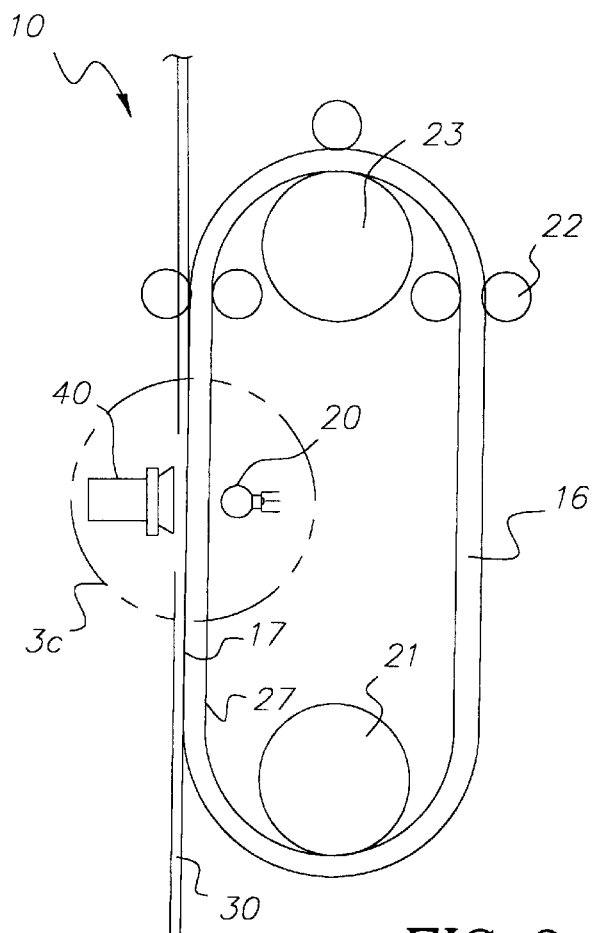
FIGS. 3a, 3b, 3c represent a variant of the device described with reference to FIGS. 1 and 2.
Figure 3B:
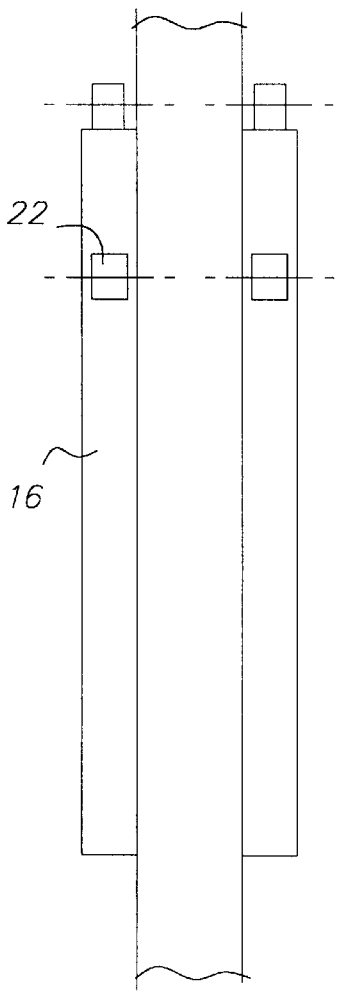

A second embodiment of the supporting and guiding device 10 of the strip 30 to be analyzed is represented by FIGS. 3a and 3b. The device 10 is transparent to light rays, generally plastic, and it comprises a support body 16. The body 16 is sufficiently flexible to form a closed path that winds around at least one motor roller 21, 23 whose rotation speed is synchronous with the running speed of the strip 30, so that the filmstrip 30 runs by pressing on a flat surface 17 of the support body 16 without there being any relative slippage between the strip 30 and the flat surface 17. The support body 16, with relatively low total thickness, is made of practically transparent plastic and comprises two mirror polished surfaces 17, 27 that are opposed and parallel, with widths more than the width of the strip 30, having a flatness tolerance in the order of 0.05 mm. The surface 17 taking the strip 30 is flat because it is guided by means, like for instance holding rollers 22, or bearing cages, or a rollers/ball-bearing components combination. The guiding of the flat surface 17 must provide the flatness of the surface 17 in the zone of the light beam emitted by the light source 20. The support body 16 also comprises a thin screen 18 in liquid crystals provided with opaque zones 19, the forming and dimensions of the opaque zones being programmed so as to coincide practically completely with the perforations of the strip 30 to be analyzed and the opaque crown zones previously defined, which is to prevent significant disturbance and deterioration of the recording and thus of the later analysis, the disturbance and deterioration being due to the light rays that cross the perforations of the strip 30 to be analyzed and that dazzle the recording device.

One variant of this second embodiment includes substituting the thin screen 18 by a strip constituting a negative mask of the strip 30 to be analyzed.

A third embodiment includes running the strip 30 in front of a fixed device comprising a thin screen 18 in liquid crystals provided with opaque zones 19; the functioning of the screen 18 being managed in synchronization with the running of the strip 30 to be analyzed; which is in order to mask the perforations of the strip 30 and the previously defined crown zones.

Figure 3C:
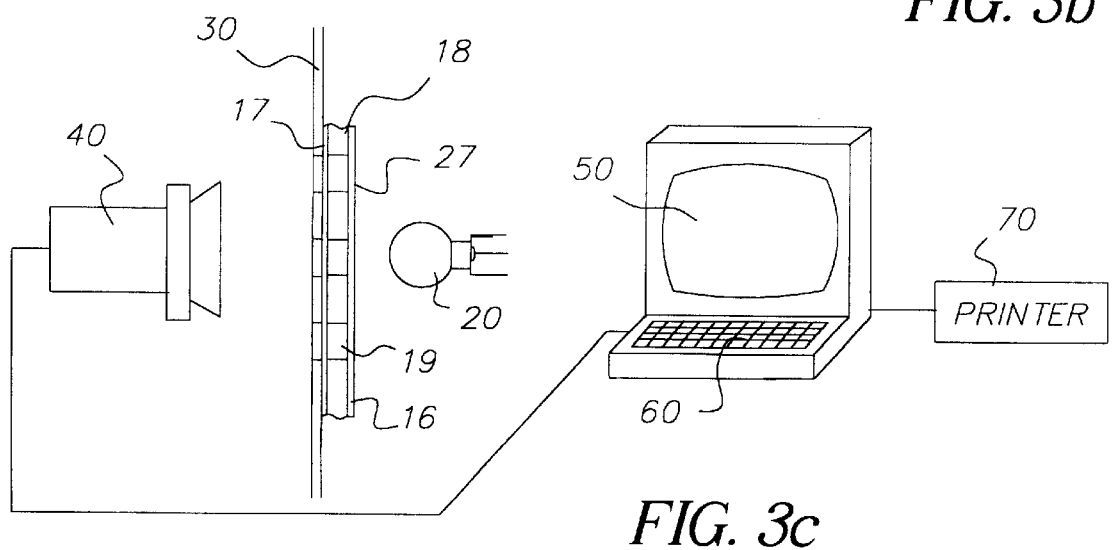

The light source 20 or the recording device 40 can be placed equally well and respectively, either inside, or outside the closed path generated by the support body 16 and shown in FIG. 3a–3c; the elements 20 and 40 can thus be placed equally well and respectively either on the support body 16 side, or on the side opposite the support body 16, in relation to the strip 30. The condition to be respected is that the elements 20 and 40 are located in the same alignment and respectively on either side of the assembly constituted by the support body 16 and the strip 30 to be analyzed. One preferred variant of this embodiment shall be to place the light source 20 on the side of the thin screen 18 in liquid crystals 19, and the recording device 40 on the side of the strip 30 to be analyzed, as shown in FIG. 3c.

The invention has been described in detail with particular reference to certain preferred embodiments thereof, but it will be understood that variations and modifications can be effected within the spirit and scope of the invention.

What is claimed is:

1. An automatic machine for analyzing a surface cleanness condition of relatively transparent strips, the machine comprising:

a structure and electromechanical components adapted to hold and convey at least one strip to be analyzed;

a light source adapted to light the at least one strip;

a recording device adapted to detect, record and view the surface of said at least one strip; and a supporting and guiding device for supporting and guiding said at least one strip while in a lighting and recording zone, said supporting and guiding device enabling a substantial masking of perforations made in said at least one strip when it runs in the automatic machine.

2. A machine according to claim 1, wherein the support and guiding device comprises:

a revolving member which comprises a material that enables a transmission of light and has an external surface that can support the at least one strip to be analyzed, said external surface being polished and provided with opaque masks in a thin layer, and being arranged so that there is superimposition of said opaque masks in the thin layer with the perforations of the at least one strip; and a driving device for driving the revolving member which enables a rotation of said revolving member to be servo-linked to a drive train of a running system for the at least one strip, so that a relative movement between the rotation of the revolving member and the running of the at least one strip occurs without slippage.

3. A machine according to claim 2, wherein the driving device of the revolving member is a shaft that is coaxial with said revolving member.

4. A machine according to claim 1, wherein said supporting and guiding device comprises a support for the at least one strip, transparent to light rays emitted by the light source, and adapted to run in front of the light source without synchronous slippage with the at least one strip, said support comprising:

a flat surface in a beam zone of the light rays emitted by the light source and enabling reception of the at least one strip; and a thin screen with liquid crystals, practically parallel and near said flat surface, the screen being configured to trap or stop practically completely at least the light rays emitted by the light source in a direction of the perforations of the at least one strip.

* * * * *